(12) United States Patent
Suzuki (10) Patent No.: US 6,942,642 B2
(45) Date of Patent: Sep. 13, 2005

(54) RETAINING NEEDLE WITH WING

(75) Inventor: Takashi Suzuki, Tokyo (JP)

(73) Assignee: Kabushiki Kaisha Top, Tokyo (JP)

( * ) Notice: Subject to any disclaimer, the term of this patent is extended or adjusted under 35 U.S.C. 154(b) by 210 days.

(21) Appl. No.: 10/416,327

(22) PCT Filed: Jul. 26, 2002

(86) PCT No.: PCT/JP02/07591

§ 371 (c)(1),
(2), (4) Date: May 8, 2003

(87) PCT Pub. No.: WO03/026725

PCT Pub. Date: Apr. 3, 2003

(65) Prior Publication Data

US 2004/0044310 A1 Mar. 4, 2004

(30) Foreign Application Priority Data

Sep. 20, 2001 (JP) ........................................ 2001-287689

(51) Int. Cl.[7] ........................... A61M 5/00; A61M 5/178
(52) U.S. Cl. ...................................... 604/110; 604/263
(58) Field of Search ................................ 604/110, 263, 604/177, 165.03

(56) References Cited

U.S. PATENT DOCUMENTS

| 5,067,946 A | 11/1991 | Zhadanov |
| 5,928,199 A | 7/1999 | Nakagami |
| 6,228,066 B1 | 5/2001 | Zhadanov et al. |

FOREIGN PATENT DOCUMENTS

| EP | 1048311 A2 | 11/2000 |
| GB | 3258 | 3/1899 |
| GB | 1188579 | 4/1970 |
| JP | 3198492 | 6/2001 |
| JP | 2001-245980 A | 9/2001 |
| WO | 00/56384 A1 | 9/2000 |

*Primary Examiner*—Sharon Kennedy
(74) *Attorney, Agent, or Firm*—Birch Stewart Kolasch & Birch LLP (57) ABSTRACT

There is here provided an easily operable winged indwelling needle capable of surely preventing accidental sticking. A winged indwelling needle 1 comprises a hollow needle 2 having a knife point at its tip, a hub 3 provided at a rear end of the hollow needle 2, a tub-shaped member 6 for housing the hollow needle 2 and the hub 3, a pair of wing-shaped members 7 provided on an outer surface side of a side wall of the tub-shaped member 6, protrusion maintaining means for releasably maintaining a state in which the hollow needle 2 is protruded as much as a predetermined length from a tip of the tub-shaped member 6, and housing maintaining means for maintaining a state in which the hollow needle 2 is housed in the tub-shaped member 6. The above winged indwelling needle further comprises a rack 4 provided in junction with the rear end of the hub 3, and a gear 8 engaged with the rack and supported on an inner surface side of the side wall of the tub-shaped member 6. The hollow needle 2 is driven through the rack 4 by rotating the gear 8 to be housed in the tub-shaped member 6.

10 Claims, 4 Drawing Sheets

RETAINING NEEDLE WITH WING

This application is the national phase under 35 U.S.C. § 371 of PCT International Application No. PCT/JP02/07591 which has an International filing date of Jul. 26, 2002, which designated the United States of America.

TECHNICAL FIELD

The present invention relates to a winged indwelling needle which is used for temporarily securing a venous path or the like.

BACKGROUND ART

As a needle used for a medical practice such as temporary securing of a venous path, a winged indwelling needle has conventionally been known, which comprises a hollow needle, a hub for holding a rear end of the hollow needle, and a pair of wing-shaped members formed integrally with the hub. When the winded indwelling needle is used, a medical personnel such as a doctor or a nurse first removes a protector attached to the hollow needle, grips the pair of wing-shaped members in a superposed manner, and then sticks the hollow needle into a vein of a patient. Then, he fixes the hollow needle by opening the pair of wing-shaped members, and pasting them to a body surface of the patient by adhesive tape or the like.

After used, the winged indwelling needle is pulled out, and disposed of. In this case, if the hollow needle is exposed, the medical personnel or a worker engaged in disposal (abbreviated to medical personnel, hereinafter) may stick the hollow needle into a finger or the like accidentally (abbreviated to accidental sticking, hereinafter). Here, if the patient suffers from an infectious disease such as HIV or acute hepatitis, there is a possibility that the medical personnel may be infected with the disease through the hollow needle.

Conventionally, in order to prevent such accidental sticking, recapping has been carried out, which attaches the protector removed before the use again to the used hollow needle. The conventional protector has a hollow cylindrical body provided with a length equal to that of the hollow needle. Accordingly, the recapping is carried out by approaching the protector and the hollow needle to each other in an extended direction of the hollow needle, and inserting the hollow needle from its tip into an opening end of the protector.

However, in the protector, since fingers gripping the protector are positioned in a moving direction of the tip of the hollow needle, a problem may occur, i.e., accidental sticking of the finger by the hollow needle during the recapping.

In order to solve the foregoing problem, Japanese Patent No. 3198492 discloses a winged indwelling needle, which comprises a hollow needle, a holder, into which the hollow needle is inserted, and protruded from a tip, and a pair of wing-shaped members provided in the holder. In the disclosed winged indwelling needle, a hub provided at a rear end of the hollow needle is freely engaged with the holder, and the hollow needle is protruded from the tip of the holder while the hub is in the engaged state with the holder. Accordingly, the winged indwelling needle can be fixed by sticking the hollow needle protruded from the tip of the holder into a vein of a patient, and by opening the pair of wing-shaped members and pasting them to a body surface of the patient.

To remove the hollow needle, the hollow needle is housed in the holder by disengaging the hub from the holder while the wing-shaped members are pasted to the patient, and retreating the hub. Thus, the holder becomes a protector of the hollow needle, which can prevent accidental sticking.

However, in the winged indwelling needle described in the Publication, in order to disengage the hub from the holder, the holder must be held by one hand, and a disengaging operation must be carried out by the other hand. Consequently, inconvenience, i.e., a difficulty of operation without use of two hands, still remains.

DISCLOSURE OF THE INVENTION

The present invention was made to solve the foregoing inconvenience, and it is an object of the invention to provide an easily operable winged indwelling needle capable of surely preventing accidental sticking.

In order to achieve the object, a winged indwelling needle of the present invention comprises a hollow needle having a knife point at its tip, a hub provided at a rear end of the hollow needle, a tub-shaped member for housing the hollow needle and the hub slidingly in a longitudinal direction, a pair of wing-shaped members provided on an outer surface side of a side wall of the tub-shaped member, protrusion maintaining means for releasably maintaining a state in which the hollow needle is protruded as much as a predetermined length from a tip of the tub-shaped member, and housing maintaining means for maintaining a state in which the hollow needle is housed in the tub-shaped member, the above winged indwelling needle further comprising a rack provided in junction with the rear end of the hub, and a gear engaged with the rack and supported on an inner surface side of the side wall of the tub-shaped member, the hollow needle being driven through the rack by rotating the gear to be housed in the tub-shaped member.

According to the winged indwelling needle of the present invention, first, a medical personnel such as a doctor or a nurse grips the tub-shaped member, or the pair of the wing-shaped members in a superposed manner, and sticks the hollow needle into a patient. At this time, the hollow needle is maintained in the state of being protruded from the tip of the tub-shaped member by the predetermined length by the protrusion maintaining means. As a result, since the hollow needle is maintained in the state of being protruded from the tip of the tub-shaped member, and not moved forward/backward, a needle point is never moved, thereby facilitating the sticking operation.

In the winged indwelling needle, after the hollow needle is stuck into the patient, the hollow needle is fixed by opening the wing-shaped members, and pasting them to a body surface of the patient by adhesive tape or the like. At this time, the protrusion maintaining means regulates retreating of the hollow needle, making it possible to prevent the hollow needle from being pulled out from the patient.

When the hollow needle is pulled out from the body of the patient, first, the regulation by the protrusion maintaining means is released. Then, the tub-shaped member is held by one hand. When the gear is rotated by fingers of the hand gripping the tub-shaped member, the gear drives the hollow needle through the rack, and the hollow needle is housed in the tub-shaped member. Then, by using the housing maintaining means, the hollow needle is maintained in the state of being housed in the tub-shaped member at a position where the tip of the hollow needle is housed in the tub-shaped member. As a result, it is possible to prevent the hollow needle from being protruded again from the tip of the tub-shaped member.

After the hollow needle is housed in the tub-shaped member, the tub-shaped member operates as a protector, thereby preventing the finger of the medical personnel from touching the hollow needle.

According to the winged indwelling needle of the present invention, the conventional necessity of approaching the protector and the hollow needle to each other by both hands, and inserting the hollow needle into the opening of the protector is eliminated, making it possible to surely prevent accidental sticking. Moreover, in the winged indwelling needle of the invention, since the gear is rotated by one hand to house the hollow needle in the tub-shaped member, thus facilitating an operation.

In accordance with a first mode, the protrusion maintaining means comprises, for example, a first extension member provided at the rear end of the rack to be extended in a direction along the side wall, and a locking member which is provided to freely open and close the rear end of the tub-shaped member and which locks a rear end of the extension member so as to maintain a state in which the hollow needle is protruded as much as a predetermined length from the tip of the tub-shaped member when the rear end of the tub-shaped member is closed. Alternatively, in accordance with a second mode, the protrusion maintaining means comprises a first handle integrally attached to the gear rotatably together with the gear, and a first protruded portion provided on an inner surface side of the side wall at the rear end of the tub-shaped member to detachably lock the first handle at a position where the hollow needle is protruded as much as a predetermined length from the tip of the tub-shaped member.

In accordance with a first mode, the housing maintaining means comprises, for example, a second protruded portion provided to be protruded from the tip of the rack to its side, and an engaging concave portion provided on the inner surface side of the side wall at the rear end of the tub-shaped member and engaged with the second protruded portion so as to maintain a state in which the hollow needle is housed in the tub-shaped member. Alternatively, in accordance with a second mode, the housing maintaining means comprises a second handle integrally attached to the gear rotatably together with the gear, and a third protruded portion provided on the inner surface side of the side wall in the tip of the tub-shaped member to detachably lock the second handle at a position where the hollow needle is housed in the tub-shaped member. In the second mode of the housing maintaining means, the second handle preferably comprises, on its tip, a branch portion which is arranged in front of the knife point of the hollow needle when the second handle is engaged with the third protruded portion.

The first and second modes of the protrusion maintaining means, and the first and second modes of the housing maintaining means can be freely combined with each other. Moreover, when the second mode of the protrusion maintaining means is combined with the second mode of the housing maintaining means, preferably, the first and second handles are constructed similarly to each other.

In the winged indwelling needle of the present invention, the rack preferably comprises a second extension member extended from the rear end to the side to lock a rear end surface of the tub-shaped member, thereby preventing the tub-shaped member from moving behind the rack. According to the second extension member, the operation of sticking the hollow needle into the patient can be performed more stably by preventing the tub-shaped member from being moved behind the rack.

BEST MODES FOR CARRYING OUT THE INVENTION

First, description will be made of a first embodiment of the present invention.

Figure 1:
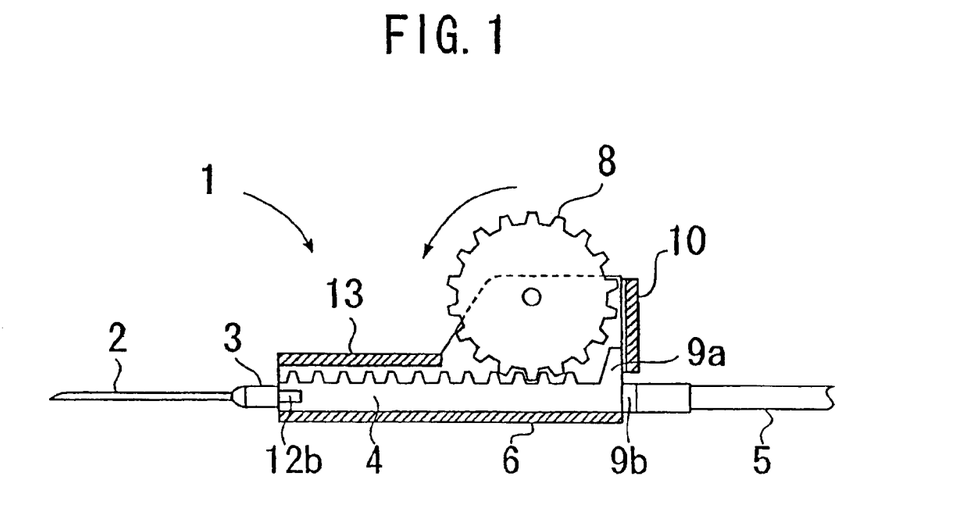
FIG. 1 is an explanatory sectional view showing constitution of a winged indwelling needle according to a first embodiment of the present invention.
Figure 2:
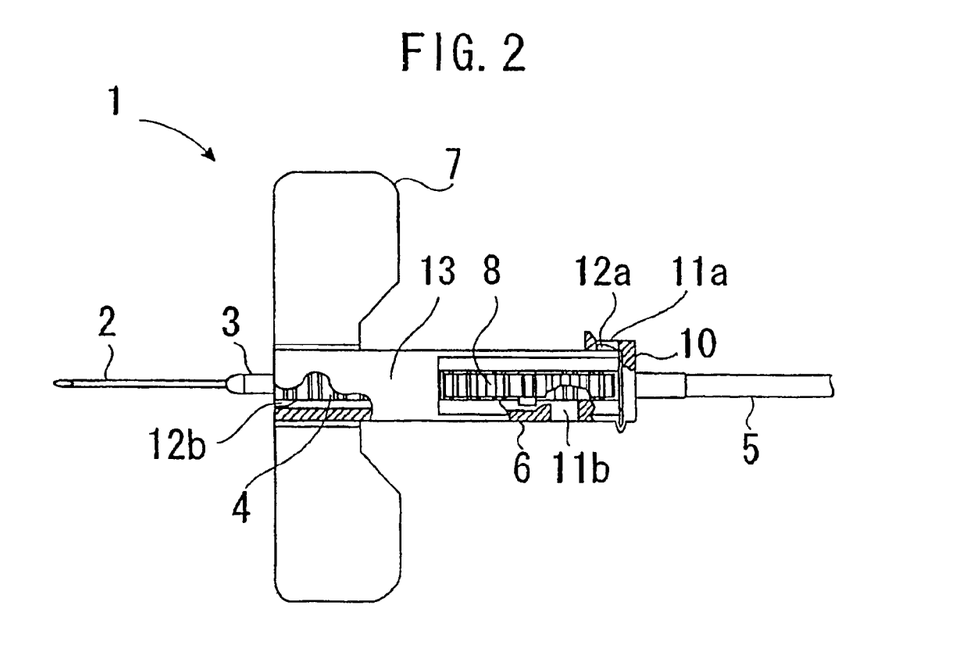
FIG. 2 is a partially cutout plan view of the winged indwelling needle shown in FIG. 1.

As shown in FIGS. 1 and 2, a winged indwelling needle 1 of the present invention comprises a hollow needle 2 having a knife point on its tip, and a hub 3 provided at a rear end of the hollow needle 2. A hollow rack 4 is provided in junction with a rear end of the hub 3. A tube 5 is connected to a rear end of the rack extended in a rear direction, which guides drug solution through the hub 3 and the rack 4 to the hollow needle 2.

The hub 3 and the rack 4 are housed in a tub-shaped member 6 so as to be freely slid in a longitudinal direction therein. The tub-shaped member 6 is made of a synthetic resin and, an outer surface side of a side wall, a pair of wing-shape members 7 are horizontally provided integrally. The tube 5 may be inserted into the rack 4, and connected to the hub 3.

The tub-shaped member 6 has two side walls extended upward on both sides of the housed rack 4. Between the side walls, a gear 8 engaged with the rack 4 is supported. An upper portion of the gear 8 is exposed from upper edges of both side walls of the tub-shaped member 6 indicated by a chain line in FIG. 1, so as to be freely rotated.

In the tub-shaped member 6, a portion above the rack 4 is opened in a part where the gear 8 is provided. In a tip portion not in contact with the gear 8, an upper surface is sealed to form a cylindrical portion 13.

At a rear end of the rack 4, an extension member 9a is provided to be extended upward. On the other hand, at a rear end of the sub-shaped member 6, a locking member 10 L-shaped on plane is provided in junction so as to be bent freely in a position for contact with the extension member 9a in the upper side of the rack 4 on one side of the side wall. An engaging concave portion 11a is provided in a tip of the locking member 10 so as to be freely engaged with a protruded portion 12a protruded on an outer surface side of the other side wall of the tub-shaped member 6. The protruded portion 12a is formed to have a tapered rear side, and a surface of a tip perpendicular to the side wall.

As a result, by engaging the engaging portion 11a with the protruded portion 12a, the locking member 10 locks the extension member 9a, and regulates retreating of the rack 4. That is, the present invention constructs a first mode of protrusion maintaining means for maintaining a state of the hollow needle 2 being protruded from the tip of the tub-shaped member 6 by a predetermined length by the extension member 9a and the locking member 10.

In this case, if the rack 4 is disengaged from the gear 8, the tub-shaped member 6 may be retreated with respect to the position of the rack 4, making it impossible to fix the hollow needle 2 to the wing-shaped member 7. Thus, in the embodiment, an extension member 9b is provided at a rear end of the rack 4, which is extended in a side face direction. By locking the rear end surface of the tub-shaped member 6, the extension member 9b can regulate the tub-shaped member 6 to prevent its retreating with respect to the rack 4.

On a tip side face of the rack 4, a protruded portion 12a is formed to have a tapered rear side, and a tip surface perpendicular to the side wall. On the other hand, at the rear end of the tub-shaped member 6, on an inner surface side of the side wall, in a position opposite the side face of the rack 4, an engaging concave portion 11b is provided to have a tapered tip, and a surface perpendicular to the inner surface side of the side wall after the tapered portion.

As a result, when the hollow needle 2 is housed in the tub-shaped member 6, the rack 4 is regulated for forward/backward movement by engaging the perpendicular surface of the protruded portion 12b with the perpendicular surface of the engaging portion 11b. That is, the embodiment forms a first mode of housing maintaining means for maintaining a state of the hollow needle 2 being housed in the tub-shaped member 6 by engaging the protruded portion 12b with the engaging portion 11b.

Next, description is made of a method for using the winged indwelling needle 1 of the embodiment by referring to FIGS. 1 to 4.

To use the winged indwelling needle 1 of the embodiment, the medical personnel first grips the tub-shaped member 6, or the pair of wing-shaped members 7 in a superposed manner, and sticks the hollow needle 2 protruded from the tub-shaped member 6 into a patient.

Then, the medical personnel expands the pair of wing-shaped members 7, and retains the hollow needle 2 by pasting them to a body surface of the patient to fix the hollow needle 2. As a result, a venous path is temporarily secured by the hollow needle 2. Then, drug administration is carried out by introducing drug solution or the like from the tube 5 through the hollow needle 2 into a vein.

When the hollow needle 2 is retreated during the sticking or retaining, the extension member 9a provided at the rear end of the rack 4 is locked by the locking member 10. As a result, it is possible to maintain the state of the hollow needle 2 being protruded from the tip of the tub-shaped member 6 by a predetermined length by blocking the retreating of the hollow needle 2. In addition, during the retaining of the hollow needle 2, the extension member 9b locks the rear end surface of the tub-shaped member 6, thereby preventing the tub-shaped member 6 from being retreated with respect to the position of the hollow needle 2. Therefore, the hollow needle 2 is surely fixed by pasting the wing-shaped members 7, making it possible to perform the operation such as drug administration in a stable manner.

To remove the hollow needle 2, and house it in the tub-shaped member 6, the medical personnel first operates the engaging portion 11a of the locking member 10, and moves it in a direction away from the side wall surface of the tub-shaped member 6. As a result, the engagement between the protruded portion 12a and the locking member 11a is released, the extension member 9a is not regulated by the locking member 10, and the rack 4 is freely moved to the rear side of the tub-shaped member 6.

Figure 3:
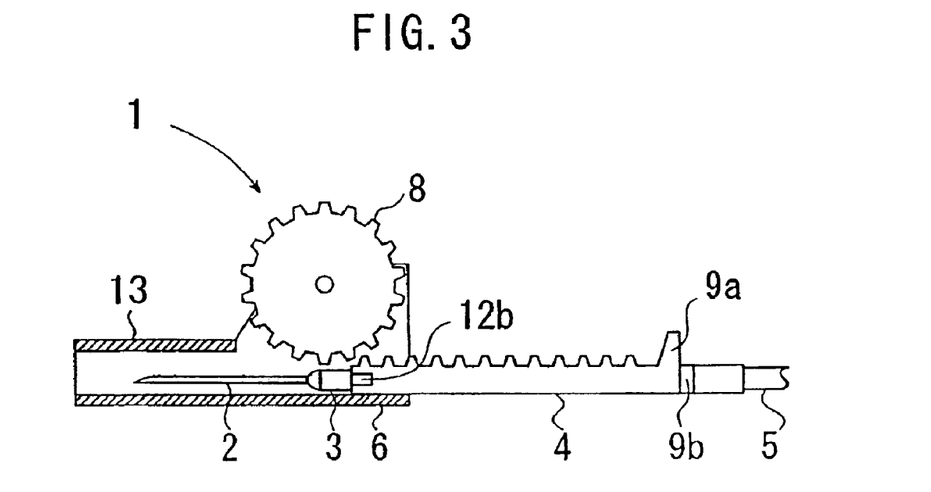
FIG. 3 is an explanatory sectional view showing an operation of the winged indwelling needle shown in FIG. 1.
Figure 4:
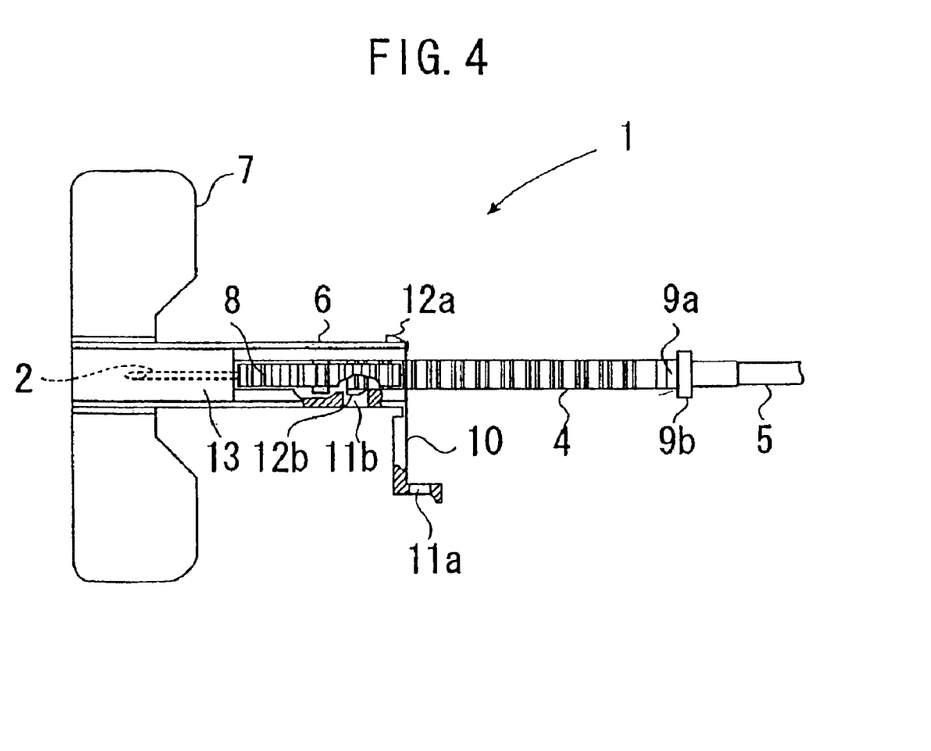
FIG. 4 is an explanatory partially cutout plan view showing an operation of the winged indwelling needle shown in FIG. 1.

Then, as indicated by an arrow in FIG. 1, the medical personnel rotates the gear 8 toward the tip of the hollow needle 2 by a finger. Upon the rotation of the gear 8, the rack 4 engaged with the gear 8 is driven to be retreated, and the hollow needle 2 is retreated as shown in FIGS. 3 and 4.

After the tip of the hollow needle 2 has been retreated to the position of being housed in the tub-shaped member 6, the protruded portion 12b provided on the outer surface side of the side wall of the rack 4 is engaged with the engaging portion 11b provided on the inner surface side of the side wall of the tub-shaped member 6. In this case, the protruded portion 12b has a tapered rear end. Thus, the rear end of the protruded portion 12b is guided by the tapered portion provided in the tip of the engaging portion 11b to be moved in a rear direction, and engaged with the concave portion of the engaging portion 11b after going over the tapered portion.

Therefore, the winged indwelling needle 1 can maintain the state of the hollow needle 2 being housed in the tub-shaped member 6 and, once housed in the tub-shaped member 6, the hollow needle 2 is never protruded again from the tip of the tip of the tub-shaped member 6. Thus, it is possible to prevent the medical personnel from accidentally sticking the hollow needle 2 protruded from the tip of the tub-shaped member 6.

Furthermore, since the tub-shaped member 6 has the cylindrical portion 13 formed on its tip, the tip of the housed hollow needle 2 is surrounded with the cylindrical portion 13. Thus, it is possible to surely prevent the finger of the medical personnel or the like from touching the tip of the hollow needle 2 contaminated with blood or the like of the patient.

Next, description is made of a second embodiment of the present invention.

Figure 5:
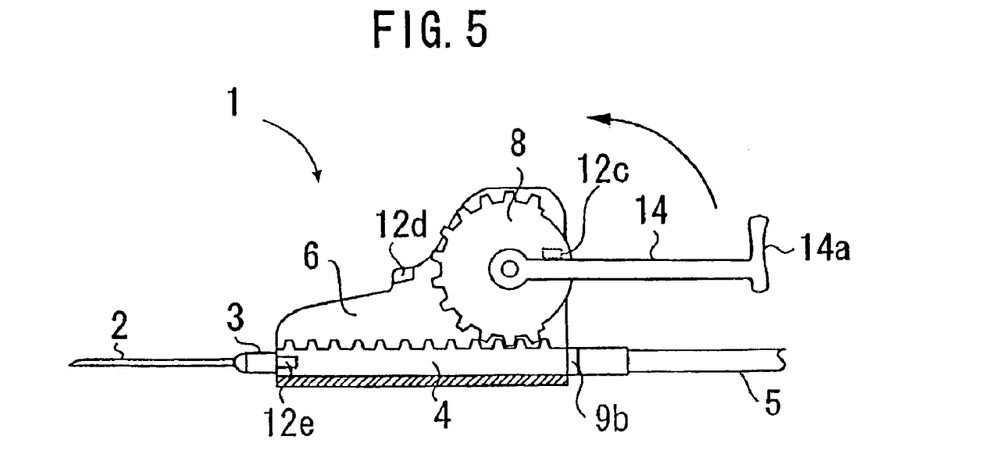
FIG. 5 is an explanatory sectional view showing a winged indwelling needle according to a second embodiment of the present invention.
Figure 6:
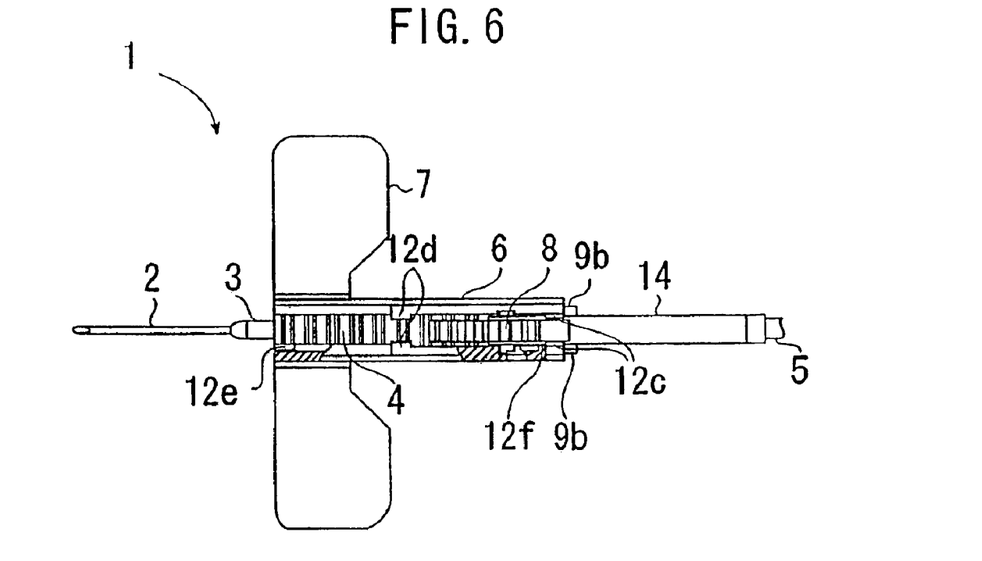
FIG. 6 is a partially cutout plan view of the winged indwelling needle shown in FIG. 5.

As shown in FIGS. 5 and 6, a winged indwelling needle 1 according to a second embodiment of the present invention is completely similar in constitution to the winged indwelling needle 1 of the first embodiment except the protrusion maintaining means and the housing maintaining means. Thus, similar components are denoted by similar reference numerals, and detailed description thereof will be omitted.

The second embodiment employs a second mode, where the protrusion maintaining means includes an L-shaped handle 14 integrally attached to the gear 8, and associatively rotated therewith, and a protruded portion 12c provided at a rear end of the tub-shaped member 6 to detachably lock the L-shaped handle 14. The protruded portion 12c is provided to be protruded on the inner surface side of the side wall at the rear end of the tub-shaped member 6. The protruded portion 12c locks the L-shaped handle 14, and regulates rotation of the L-shaped handle 14 toward the tip of the tub-shaped member 6.

The second embodiment employs a second mode, where the housing maintaining means includes the L-shaped handle 14, and a protruded portion 12d provided in the tip of the tub-shaped member 6 to detachably lock the L-shaped handle 14. The protruded portion 12d is provided to be protruded on the inner surface side of the side wall in the tip of the tub-shaped member 6. The protruded portion 12d locks the L-shaped handle 14, and regulates rotation of the L-shaped handle 14 in the rear end direction of the tub-shaped member 6.

In this case, if the rack 4 is disengaged from the gear 8, the hollow needle 2 may be pulled out from the rear end of the tub-shaped member 6, the tub-shaped member 6 may not be operated as a protector. Thus, in the embodiment, a protruded portion 12e is provided to be protruded from the tip of the rack 4 to the side, and a protruded portion 12f provided on the inner surface side of the side wall at the rear end of the tub-shaped member 6. As a result, when the hollow needle 2 is housed in the tub-shaped member 6, the protruded portion 12e of the rack 4 is locked by the protruded portion 12f of the tub-shaped member 6, thereby preventing the hollow needle 2 from being pulled out.

In the winged indwelling needle 1 of the embodiment, the tub-shaped member 6 has an opening above the rack 4 on a full length, and the side wall of the tub-shaped member 6 substantially covers the gear 8 excluding the L-shaped handle 14. The L-shaped handle 14 includes a branch portion formed on its tip.

Next, description is made of a method for using the winged indwelling needle 1 of the embodiment by referring to FIGS. 5 and 6.

In the winged indwelling needle 1 of the embodiment, completely similarly to the first embodiment, the hollow needle 2 is stuck into the patient, fixed and retained. Then, drug administration is carried out through the tube 5.

In this case, if the hollow needle 2 is retreated, the gear 8 engaged with the rack 4 is rotated toward the tip of the hollow needle 2. However, the L-shaped handle 14 integrally attached to the gear 8 is locked by the protruded portion 12c. As a result, the L-shaped handle 14 locked in the protruded portion 12c regulates rotation of the gear 8 to block retreating of the hollow needle 2, making it possible to maintain the state of the hollow needle 2 being protruded from the tip of the tub-shaped member 6 by a predetermined length. In addition, during the retaining of the hollow needle 2, completely similarly to the first embodiment, the extension member 9b locks the rear end surface of the tub-shaped member 6. Thus, the hollow needle 2 is surely fixed by pasting the wing-shaped members 7, making it possible to perform the operation such as drug administration in a stable manner.

To remove the hollow needle 2, and house it in the tub-shaped member 6, the medical personnel first grips the L-shaped handle 14, and rotates the hollow needle toward to a tip as indicated by an arrow in FIG. 5. Since the tub-shaped member 6 and the protruded portion 12c are made of synthetic resins, by applying a predetermined force or more to the L-shaped handle 14, the protruded portion 12c abutted on the L-shaped handle 14 is widened toward the side wall of the tub-shaped member 6. Thus, the L-shaped handle 14 can be rotated toward the tip of the hollow needle 2 after going over the protruded portion 12c.

Figure 7:
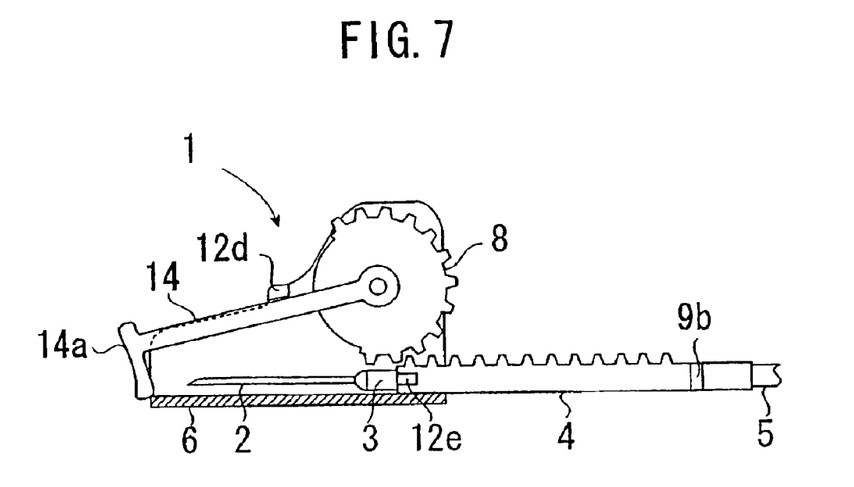
FIG. 7 is an explanatory sectional view showing an operation of the indwelling needle shown in FIG. 5.
Figure 8:
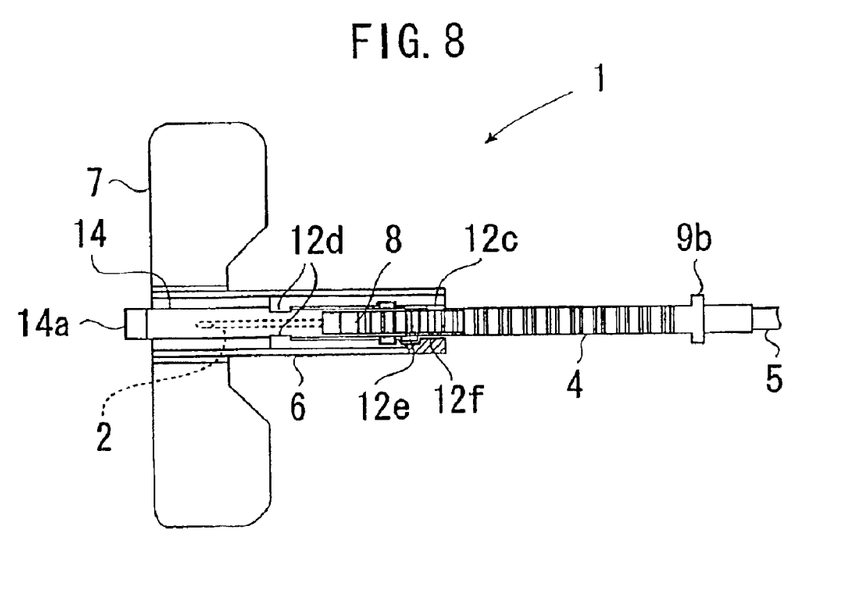
FIG. 8 is an explanatory partially cutout plan view showing an operation of the indwelling needle shown in FIG. 5.

Then, when the L-shaped handle 14 is gripped, and rotated in a direction indicated by an arrow in FIG. 5, since the L-shaped handle 14 is integrally attached to the gear 8, the gear 8 is also rotated associatively. As a result, the rack 4 engaged with the gear 4 is driven to be retreated, and the hollow needle 2 is retreated as shown in FIGS. 7 and 8.

After the tip of the hollow needle 2 has been retreated to the position of being housed in the tub-shaped member 6, by applying a predetermined force or more to the L-shaped handle 14, the protruded portion 12d abutted on the L-shaped handle 14 is widened toward the side wall of the tub-shaped member 6. Then, the L-shaped handle 14 is locked on the bottom surface of the protruded portion 12d after going over the protruded portion 12d. As a result, the winged indwelling needle 1 can maintain the state of the hollow needle 2 being housed in the tub-shaped member 6 and, once housed in the tub-shaped member 6, the hollow needle 2 is never protruded again from the tip of the tub-shaped member 6. Therefore, it is possible to prevent the medical personnel or the like from accidentally sticking the hollow needle 2 protruded from the tip of the tub-shaped member 6.

Furthermore, in a state where the L-shaped handle 14 is locked on the bottom surface of the protruded portion 12d, the branch portion 14a is arranged in front of the knife point of the hollow needle 2 in the tub-shaped member 6. As a result, in the tub-shaped member 6, the opening surface above the rack 4, and the tip opening as a path for protrusion of the hollow needle 2 are covered with the L-shaped handle 14.

Thus, it is possible to surely prevent the finger of the medical personnel or the like from touching the tip of the hollow needle 2 contaminated with blood or the like of the patient. Moreover, by the branch portion 14a, it is possible to surely prevent the hollow needle 2 from being protruded again from the tip of the tub-shaped member 6.

After the hollow needle 2 has been housed in the tub-shaped member 6, the protruded portion 12e provided on the side face in the tip of the rack 4 is locked by the protruded portion 12f provided on the inner surface side of the side wall at the rear end of the tub-shaped member 6. Thus, it is possible to prevent the hollow needle 2 housed in the tub-shaped member 6 from being further retreated to fall off from the tub-shaped member 6.

To prevent the falling-off of the hollow needle 2 from the tub-shaped member 6, means may be provided for maintaining engagement between the rack 4 and the gear 4 when the hollow needle 2 is housed in the tub-shaped member 6.

In each of the foregoing embodiments, the first mode of the protrusion maintaining means is combined with the first mode of the housing maintaining means, and the second modes thereof are combined with each other. However, the first mode of the protrusion maintaining means may be connected to the second mode of the housing maintaining means. The second mode of the protrusion maintaining means may be combined with the first mode of the housing maintaining means.

INDUSTRIAL APPLICABILITY

The present invention can be applied to a winged indwelling needle used for temporarily securing a venous path or the like.

What is claimed is:

1. A winged indwelling needle comprising:

a hollow needle having a knife point at its tip, a hub provided at a rear end of the hollow needle, a tub-shaped member for housing the hollow needle and the hub slidingly in a longitudinal direction, a pair of wing-shaped members provided on an outer surface side of a side wall of the tub-shaped member, protrusion maintaining means for releasably maintaining a state in which the hollow needle is protruded as much as a predetermined length from a tip of the tub-shaped member, and housing maintaining means for maintaining a state in which the hollow needle is housed in the tub-shaped member, said winged indwelling needle further comprising a rack provided in junction with the rear end of the hub, and a gear engaged with the rack and supported on an inner surface side of the side wall of the tub-shaped member, said hollow needle being driven through the rack by rotating the gear to be housed in the tub-shaped members, wherein the housing maintaining means comprises a second protruded portion provided to be protruded from the tic, of the rack to its side, and an engaging concave portion provided on the inner surface side of the side wall at the rear end of the tub-shaped member and engaged with the second protruded portion so as to maintain a state in which the hollow is housed in the tub-shaped member.

2. The winged indwelling needle according to claim 1, wherein the protrusion maintaining means comprises a first extension member provided at the rear end of the rack to be extended in a direction along the sidewall, and a locking member which is provided to freely open and close the rear end of the tub-shaped member and which locks a rear end of the extension member so as to maintain a state in which the hollow needle is protruded as much as a predetermined length from the tip of the tub-shaped member when the rear end of the tub-shaped member is closed.

3. The winged indwelling needle according to claim 1, wherein the protrusion maintaining means comprises a first handle integrally attached to the gear rotatably together with the gear, and a first protruded portion provided on an inner surface side of the side wall at the rear end of the tub-shaped member to detachably lock the first handle at a position where the hollow needle is protruded as much as a predetermined length from the tip of the tub-shaped member.

4. The winged indwelling needle according to claim 1, wherein the rack comprises a second extension member extended from the rear end to the side to lock a rear end surface of the tub-shaped member, thereby preventing the tub-shaped member from moving behind the rack.

5. A winged indwelling noodle needle, comprising:
a hollow needle having a knife point at its tip,
a hub provided at a rear end of the hollow needle,
a tub-shaped member for housing the hollow needle and the hub slidinaly in a longitudinal direction,
a pair of wing-shaped members provided on an outer surface side of a sidewall of the tub-shaped member,
protrusion maintaining means for releasably maintaining a state in which the hollow needle is protruded as much as a predetermined length from a tip of the tub-shaped member, and
housing maintaining means for maintaining a state in which the hollow needle is housed in the tub-shaped member, said winged indwelling needle further comprising a rack provided in junction with the rear end of the hub, and a gear engaged with the rack and supported on an inner surface side of the side wall of the tub-shaped member, said hollow needle being driven through the rack by rotating the gear to be housed in the tub-shaped member,
wherein the housing maintaining means comprises a second handle integrally attached to the gear rotatably together with the gear, and a third protruded portion provided on the inner surface side of the side wall in the tip of the tub-shaped member to detachably lock the second handle at a position where the hollow needle is housed in the tub-shaped member.

6. The winged indwelling needle according to claim 5, wherein the second handle comprises, on its tip, a branch portion which is arranged in front of the knife point of the hollow needle when the second handle is engaged with the third protruded portion.

7. The winged indwelling needle according to claim 5, wherein the housing maintaining means comprises a fourth protruded portion provided on the side of the rack, and a fifth protruded portion on the inner surface side of the side wall of the tub-shaped member and engaged with the fourth protruded portion at a position where the hollow needle is housed in the tub-shaped member.

8. The winged indwelling needle according to claim 5, wherein the rack comprises a second extension member extended from the rear end to the side to lock a rear end surface of the tub-shaped member, thereby preventing the tub-shaped member from moving behind the rack.

9. The winged indwelling needle according to claim 5, wherein the protrusion maintaining means comprises a first extension member provided at the rear end of the rack to be extended in a direction along the side wall, and a locking member which is provided to freely open and close the rear end of the tub-shaped member and which locks a rear end of the extension member so as to maintain a state in which the hollow needle is protruded as much as a predetermined length from the tip of the tub-shaped member when the rear end of the tub-shaped member is closed.

10. The winged indwelling needle according to claim 5, wherein the protrusion maintaining means comprises a first handle integrally attached to the gear rotatably together with the gear, and a first protruded portion provided on an inner surface side of the side wall at the rear end of the tub-shaped member to detachably lock the first handle at a position where the hollow needle is protruded as much as a predetermined length from the tip of the tub-shaped member.

* * * * *

UNITED STATES PATENT AND TRADEMARK OFFICE
CERTIFICATE OF CORRECTION

PATENT NO. : 6,942,642 B2
DATED : September 13, 2005
INVENTOR(S) : Takashi Suzuki

It is certified that error appears in the above-identified patent and that said Letters Patent is hereby corrected as shown below:

Column 8,
Line 66, please change "tic, of the rack" to -- tip of the rack --.

Column 9,
Line 28, please change "A winged indwelling noodle needle" to -- A winged indwelling needle --.

Signed and Sealed this

Twenty-ninth Day of November, 2005

JON W. DUDAS
*Director of the United States Patent and Trademark Office*